United States Patent [19]

Nordqvist et al.

[11] Patent Number: 4,608,044

[45] Date of Patent: Aug. 26, 1986

[54] COMPRESS FOR TREATMENT OF WOUNDS

[75] Inventors: Percy Nordqvist, Särö ; Erik Hylerstedt, Gothenburg, both of Sweden

[73] Assignee: Molnlycke AB, Gothenburg, Sweden

[21] Appl. No.: 352,515

[22] Filed: Feb. 26, 1982

Related U.S. Application Data

[63] Continuation of Ser. No. 177,757, Dec. 3, 1979, abandoned.

[30] Foreign Application Priority Data

Apr. 3, 1978 [SE] Sweden .................................. 7803697

[51] Int. Cl.$^4$ .................................................. A61M 35/00
[52] U.S. Cl. ...................................... 604/290; 604/304; 128/156
[58] Field of Search ................................ 128/154–156, 128/165–166, 260, 265, 268; 424/28, 145, 149, 153; 604/289–293, 303–309, 312

[56] References Cited

U.S. PATENT DOCUMENTS

| | | | |
|---|---|---|---|
| 1,504,911 | 8/1924 | Schindler-Jenny | 128/156 |
| 1,554,027 | 9/1925 | Potratz | 424/153 |
| 2,430,740 | 11/1947 | Sharples | 128/156 |
| 2,442,973 | 6/1948 | Edelstein | 424/145 |
| 2,579,367 | 12/1951 | Curtis et al. | 424/28 |
| 2,887,112 | 5/1959 | Smith | 128/803 |
| 4,166,108 | 8/1979 | Brown et al. | 424/153 |

FOREIGN PATENT DOCUMENTS 101756 10/1897 Fed. Rep. of Germany .
157133  5/1903 Fed. Rep. of Germany .

OTHER PUBLICATIONS

Kovacs, R., *Electrotherapy and Light Therapy*, 5th Ed., Lea & Febiger, Philadelphia, 1945, pp. 73–74.

*Primary Examiner*—C. Fred Rosenbaum
*Assistant Examiner*—Sherri E. Vinyard
*Attorney, Agent, or Firm*—Holman & Stern

[57] ABSTRACT

The invention refers to a compress for treatment of discharging wounds. The compress is soaked in a solution containing sodium chloride and is then dried. The dry compress is applied to the wound and is fixed with a bandage. The secretion of the wound is absorbed by the compress, thereby cleaning the wound and preventing crust formation. An antibacterial effect is also obtained. Sodium chloride and the zinc ion effect the wound bottom directly and stimulate the healing of the wound.

2 Claims, No Drawings

4,608,044

COMPRESS FOR TREATMENT OF WOUNDS

This is a continuation of application Ser. No. 177,757, filed Dec. 3, 1979, and now abandoned.

BACKGROUND OF THE INVENTION

For the treatment of chronic and infected peripheric wounds moist sodium chloride compresses are mainly used at present, i.e. compresses soaked in an isotonic or a hypertonic sodium chloride solution. These moist compresses are placed in the wound and then a common bandage is applied. Sodium chloride solution on wounds prevents crust formations and keeps the wound soft and pliable, so that joints can be bent. Besides the epithelization of the wound bottom is facilitated and the secretion from the wound is absorbed into the compress. A hypertonic sodium chloride solution also has a cleaning effect on non-vital wound tissue by osmotically "bursting" poorly vital cells. This solution to some extent also has an antibacterial effect—at least prevents the growth of several types of bacteria.

The disadvantages of this treatment are that it requires several changes a day, that it causes maceration of the wound edges and that it is difficult to perform at home.

The sodium chloride compress however has the great advantage that the patient never becomes sensibilisized by the treatment. On the contrary to this compresses treated with antibiotics, which are used to a certain extent, causes sensibilization in many cases. A new medical dressing Debrisan ®, however, has not shown sensibilization and is told to have better absorption capacity than moist sodium chloride compresses. The disadvantages of this preparation however are a very high price and that it is difficult to apply, since the active substance is a dry powder, which easily runs out from the wound.

In the German patent specification No. 577.798 a dressing material impregnated with an oxygen delivering compound, e.g. percarbonates or perborates, is described. Here the purpose however is to effect the secretion from the wound by chemically changing it when it has been absorbed in the dressing, i.e. a quite different effect to that achieved by sodium chloride.

In the German patent specification No. 112.192 is described a sanitary towel impregnated with a solution containing a compound which prevents crust formations of the blood, e.g. sodium chloride is mentioned. This patent is probably based on an important mistake, since it is a well-known fact that menstrual blood normally is fluid and does not coagulate.

This is due to the fact that the endometrium in the uterus has a high content of plasminogen activators. These provides a decomposition of the fibrin possibly formed, which keeps the coagulum together. If a disease in the woman would allow coagulum to be formed in the sanitary towel the salt content would not have any greater effect on the hardness of the coagulum.

DESCRIPTION OF THE INVENTION

According to the invention a new type of a salt compress is provided, which is prepared by immersing a compress in a solution containing sodium chloride and/or zinc salt(s), after which the compress is dried. The salt remains in the compress. The salt (sodium chloride or zinc salt) effects the wound bottom directly, at which sodium chloride is a physiologic stimulator for healing of wounds and the zinc ion affects certain enzymes positively, which are important for the healing of wounds.

The compresses, which are somewhat stiff, are carefully pressed against the wound with a spatula and are fixed with a bandage against the moist wound bottom, at which they soften at the same time as secretion from the wound is absorbed by the compress. The wound bottom is in connection herewith cleaned and crust formation is prevented, since the protein in the secretion, which is a basic substance for crust formation, will go into the compress. An antibacterial effect is also achieved, since the bacteria will follow the secretion into the compress and there will be exerted a strong osmotic effect from the salt in the compress. Since the dry compress has a good osmotic effect the risk for inflammation in and around the wound is decreased. This leads to pain easing. In other respects the dry salt compress has the same effect on the wound as conventional moist sodium chloride compresses.

They, however, have several advantages compared to moist sodium chloride compresses, since the wet handling of these and unnecessary manual work for the nursing staff in handling of salt solutions in bottles are avoided. Moreover moist sodium chloride compresses have to be changed several (3–6) times a day, while 2 changes normally is sufficient for dry salt compresses.

DESCRIPTION OF PRACTICAL TESTS

Tests have been made in the form of an open study on 15 patients with peripheric wounds of different geneses. Five patients had gangrenous wounds owing to arterial insufficience in a foot or the feet. Three patients had decubitus in the gluteal region. Four patients had wounds on an amputation stump. One patient had a chronically infected wound in the hip area on the left side after a collum fracture and operation. One patient had a chronically infected wound on the left forearm caused by pressure from a plaster bandage. One patient had a wound from radiation damage.

All wounds were discharging and infected and showed at the beginning of the test poor epithelization and granulation formation. The arterial wounds were strongly painfull. In all cases dry wounds with an improved epithelization and granulation formation were achieved within 10 days, a result which proves to be better than the experiences from treatment with moist sodium chloride compresses. In nine cases the treatment with dry sodium chloride compresses were continued during the whole process of healing, i.e. up to 40 days, without any drawbacks being noticed. It was expected that the patients would complain of pain or increased pain when the dry compress was applied to the wound. This was, however, not the case, but only as an exception and during a short time. No maceration of the wound edges occurred.

The nursing staff performing the treatment of the wounds of the patients were satisfied with the simplicity of the bandaging of the wounds. The patients were pleased with the dry salt compresses, because they usually involved only two changes a day and because the compresses did not stick to the wounds which normally causes pain when changed. Cultivation of bacteria in seven cases showed a considerable reduction of the mixed flora of bacteria in the wounds but slight or no effect on staphvlococci.

As a summary it can be stated that the dry sodium chloride compresses have proved to have an unexpectedly positive effect, i.e. several important advantages and no disadvantages compared to the conventional treatment with moist sodium chloride compresses.

The compress is delivered in a sterile packing in the usual way. As was previously mentioned also zinc salts can be used in the compress.

What I claim is:

1. In a method for treating infected discharging wounds of the type wherein a sterile, therapeutically inert compress impregnated with an isotonic or hypertonic aqueous solution consisting essentially of sodium chloride is applied to the wound, the improvement comprising drying the impregnated compress prior to application thereof to the wound to evaporate substantially all the water present and pressing the dried impregnated compress against the wound and securing the compress with a bandage.

2. The method of treating wounds according to claim 1, wherein said compress is applied to the wound with a spatula.

* * * * *